US 8,821,561 B2

(12) United States Patent
Malewicz et al.

(10) Patent No.: US 8,821,561 B2
(45) Date of Patent: Sep. 2, 2014

(54) MARKER ARRANGEMENT FOR BIFURCATION CATHETER

(75) Inventors: Andrzej Malewicz, Minneapolis, MN (US); Richard C. Gunderson, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1292 days.

(21) Appl. No.: 11/677,337

(22) Filed: Feb. 21, 2007

(65) Prior Publication Data

US 2007/0203562 A1 Aug. 30, 2007

Related U.S. Application Data

(60) Provisional application No. 60/766,149, filed on Feb. 22, 2006.

(51) Int. Cl.
*A61F 2/84* (2006.01)

(52) U.S. Cl.
USPC .......................................... 623/1.11; 606/108

(58) Field of Classification Search
USPC .................... 623/1.11, 1.35; 606/194, 108
See application file for complete search history.

(56) References Cited

U.S. PATENT DOCUMENTS

| 1,596,754 | A | 8/1926 | Moschelle |
| 3,657,744 | A | 4/1972 | Ersek |
| 3,872,893 | A | 3/1975 | Roberts |
| 4,140,126 | A | 2/1979 | Choudhury |
| 4,309,994 | A | 1/1982 | Grunwald |
| 4,385,631 | A | 5/1983 | Uthmann |
| 4,410,476 | A | 10/1983 | Redding et al. |
| 4,413,989 | A | 11/1983 | Schjeldahl et al. |
| 4,421,810 | A | 12/1983 | Rasmussen |
| 4,453,545 | A | 6/1984 | Inoue |
| 4,503,569 | A | 3/1985 | Dotter |
| 4,552,554 | A | 11/1985 | Gould et al. |
| 4,681,570 | A | 7/1987 | Dalton |
| 4,689,174 | A | 8/1987 | Lupke |

(Continued)

FOREIGN PATENT DOCUMENTS

| CA | 2318314 | 7/1999 |
| CA | 2403826 | 9/2001 |

(Continued)

OTHER PUBLICATIONS

Caputo et al., "Stent Jail: A Minimum-Security Prison," The American Journal of Cardiology, vol. 77, pp. 1226-1230, Jun. 1, 1996.

(Continued)

*Primary Examiner* — Thomas McEvoy
*Assistant Examiner* — Julie A Szpira
(74) *Attorney, Agent, or Firm* — Seager, Tufte & Wickhem LLC

(57) ABSTRACT

A catheter assembly and related methods include first and second catheter branches that are configured to travel over separate guidewires to a vessel bifurcation treatment site within a patient. The catheter branches can each include a plurality of markers. The position of markers on one catheter branch relative to the position of markers on the other catheter branch provide a visual indication of relative twist between the catheter branches, can help distinguish one catheter branch from the other, and help with visual alignment of the catheter branches relative to the vessel bifurcation.

20 Claims, 6 Drawing Sheets

(56) References Cited

U.S. PATENT DOCUMENTS

| | | | |
|---|---|---|---|
| 4,731,055 | A | 3/1988 | Melinyshyn et al. |
| 4,733,665 | A | 3/1988 | Palmaz |
| 4,739,762 | A | 4/1988 | Palmaz |
| 4,759,748 | A | 7/1988 | Reed |
| 4,762,128 | A | 8/1988 | Rosenbluth |
| 4,769,029 | A | 9/1988 | Patel |
| 4,819,664 | A | 4/1989 | Nazari |
| 4,872,874 | A | 10/1989 | Taheri |
| 4,878,495 | A | 11/1989 | Grayzel |
| 4,896,670 | A | 1/1990 | Crittenden |
| 4,900,314 | A | 2/1990 | Quackenbush |
| 4,906,244 | A | 3/1990 | Pinchuk et al. |
| 4,909,258 | A | 3/1990 | Kuntz et al. |
| 4,946,464 | A | 8/1990 | Pevsner |
| 4,957,501 | A | 9/1990 | Lahille et al. |
| 4,957,508 | A | 9/1990 | Kaneko et al. |
| 4,964,850 | A | 10/1990 | Bouton et al. |
| 4,983,167 | A | 1/1991 | Sahota |
| 4,994,071 | A | 2/1991 | MacGregor |
| 5,042,976 | A | 8/1991 | Ishitsu et al. |
| 5,054,501 | A | 10/1991 | Chuttani et al. |
| 5,059,170 | A | 10/1991 | Cameron |
| 5,059,177 | A | 10/1991 | Towne et al. |
| 5,061,240 | A | 10/1991 | Cherian |
| 5,064,435 | A | 11/1991 | Porter |
| 5,085,664 | A | 2/1992 | Bozzo |
| 5,102,403 | A | 4/1992 | Alt |
| 5,102,417 | A | 4/1992 | Palmaz |
| 5,104,404 | A | 4/1992 | Wolff |
| 5,117,831 | A | 6/1992 | Jang et al. |
| 5,122,125 | A | 6/1992 | Deuss |
| 5,135,536 | A | 8/1992 | Hillstead |
| 5,147,317 | A | 9/1992 | Shank et al. |
| 5,159,920 | A | 11/1992 | Condon et al. |
| 5,176,617 | A | 1/1993 | Fischell et al. |
| 5,192,297 | A | 3/1993 | Hull |
| 5,195,984 | A | 3/1993 | Schatz |
| 5,211,683 | A | 5/1993 | Maginot |
| 5,217,440 | A | 6/1993 | Frassica |
| 5,222,971 | A | 6/1993 | Willard et al. |
| 5,226,913 | A | 7/1993 | Pinchuk |
| 5,234,457 | A | 8/1993 | Andersen |
| 5,236,446 | A | 8/1993 | Dumon |
| 5,244,619 | A | 9/1993 | Burnham |
| 5,254,619 | A | 10/1993 | Ando |
| 5,257,974 | A | 11/1993 | Cox |
| 5,263,932 | A | 11/1993 | Jang |
| 5,282,472 | A | 2/1994 | Companion et al. |
| 5,304,220 | A | 4/1994 | Maginot |
| 5,320,605 | A | 6/1994 | Sahota |
| 5,324,257 | A | 6/1994 | Osborne et al. |
| 5,337,733 | A | 8/1994 | Bauerfeind et al. |
| 5,338,300 | A | 8/1994 | Cox |
| 5,342,295 | A | 8/1994 | Imran |
| 5,342,297 | A | 8/1994 | Jang |
| 5,342,387 | A | 8/1994 | Summers |
| 5,350,395 | A | 9/1994 | Yock |
| 5,383,892 | A | 1/1995 | Cardon et al. |
| 5,387,235 | A | 2/1995 | Chuter |
| 5,395,332 | A | 3/1995 | Ressemann et al. |
| 5,395,334 | A | 3/1995 | Keith et al. |
| 5,404,887 | A | 4/1995 | Prather |
| 5,409,458 | A | 4/1995 | Khairkhahan et al. |
| 5,413,581 | A | 5/1995 | Goy |
| 5,413,586 | A | 5/1995 | Dibie et al. |
| 5,417,208 | A | 5/1995 | Winkler |
| 5,425,765 | A | 6/1995 | Tiefenbrun et al. |
| 5,437,638 | A | 8/1995 | Bowman |
| 5,443,497 | A | 8/1995 | Venbrux |
| 5,445,624 | A | 8/1995 | Jimenez |
| 5,449,373 | A | 9/1995 | Pinchasik et al. |
| 5,449,382 | A | 9/1995 | Dayton |
| 5,456,694 | A | 10/1995 | Marin et al. |
| 5,456,712 | A | 10/1995 | Maginot |
| 5,456,714 | A | 10/1995 | Owen |
| 5,458,605 | A | 10/1995 | Klemm |
| 5,462,530 | A | 10/1995 | Jang |
| 5,476,471 | A | 12/1995 | Shifrin et al. |
| 5,489,271 | A | 2/1996 | Andersen |
| 5,489,295 | A | 2/1996 | Piplani et al. |
| 5,496,292 | A | 3/1996 | Burnham |
| 5,505,702 | A | 4/1996 | Arney |
| 5,507,768 | A | 4/1996 | Lau et al. |
| 5,507,769 | A | 4/1996 | Marin et al. |
| 5,514,154 | A | 5/1996 | Lau et al. |
| 5,514,178 | A | 5/1996 | Torchio |
| 5,522,801 | A | 6/1996 | Wang |
| 5,531,788 | A | 7/1996 | Dibie et al. |
| 5,545,132 | A | 8/1996 | Fagan et al. |
| 5,549,553 | A | 8/1996 | Ressemann et al. |
| 5,549,554 | A | 8/1996 | Miraki |
| 5,562,620 | A | 10/1996 | Klein et al. |
| 5,562,724 | A | 10/1996 | Vorwerk et al. |
| 5,562,725 | A | 10/1996 | Schmitt et al. |
| 5,562,726 | A | 10/1996 | Chuter |
| 5,569,295 | A | 10/1996 | Lam |
| 5,571,087 | A | 11/1996 | Ressemann et al. |
| 5,575,771 | A | 11/1996 | Walinsky |
| 5,575,817 | A | 11/1996 | Martin |
| 5,575,818 | A | 11/1996 | Pinchuk |
| 5,591,228 | A | 1/1997 | Edoga |
| 5,593,442 | A | 1/1997 | Klein |
| 5,607,444 | A | 3/1997 | Lam |
| 5,609,605 | A | 3/1997 | Marshall et al. |
| 5,609,625 | A | 3/1997 | Piplani et al. |
| 5,609,627 | A | 3/1997 | Goicoechea et al. |
| 5,609,629 | A | 3/1997 | Fearnot et al. |
| 5,613,949 | A | 3/1997 | Miraki |
| 5,613,980 | A | 3/1997 | Chauhan |
| 5,613,981 | A | 3/1997 | Boyle et al. |
| 5,617,878 | A | 4/1997 | Taheri |
| 5,626,600 | A | 5/1997 | Horzewski et al. |
| 5,628,788 | A | 5/1997 | Pinchuk |
| 5,632,762 | A | 5/1997 | Myler |
| 5,632,763 | A | 5/1997 | Glastra |
| 5,632,772 | A | 5/1997 | Alcime et al. |
| 5,634,902 | A | 6/1997 | Johnson et al. |
| 5,639,278 | A | 6/1997 | Dereume et al. |
| 5,643,340 | A | 7/1997 | Nunokawa |
| 5,653,743 | A | 8/1997 | Martin |
| 5,662,614 | A | 9/1997 | Edoga |
| 5,669,924 | A | 9/1997 | Shaknovich |
| 5,669,932 | A | 9/1997 | Fischell et al. |
| 5,676,696 | A | 10/1997 | Marcade |
| 5,676,697 | A | 10/1997 | McDonald |
| 5,679,400 | A | 10/1997 | Tuch |
| 5,683,451 | A | 11/1997 | Lenker et al. |
| 5,690,642 | A | 11/1997 | Osborne et al. |
| 5,693,084 | A | 12/1997 | Chuter |
| 5,693,086 | A | 12/1997 | Goicoechea et al. |
| 5,693,088 | A | 12/1997 | Lazarus |
| 5,697,971 | A | 12/1997 | Fischell et al. |
| 5,707,354 | A | 1/1998 | Salmon et al. |
| 5,709,713 | A | 1/1998 | Evans et al. |
| 5,716,365 | A | 2/1998 | Goicoechea et al. |
| 5,718,683 | A | 2/1998 | Ressemann et al. |
| 5,718,724 | A | 2/1998 | Goicoechea et al. |
| 5,720,735 | A | 2/1998 | Dorros |
| 5,723,004 | A | 3/1998 | Dereume et al. |
| 5,724,977 | A | 3/1998 | Yock et al. |
| 5,728,158 | A | 3/1998 | Lau et al. |
| 5,733,303 | A | 3/1998 | Israel et al. |
| 5,735,893 | A | 4/1998 | Lau et al. |
| 5,746,766 | A | 5/1998 | Edoga |
| 5,749,825 | A | 5/1998 | Fischell et al. |
| 5,749,848 | A | 5/1998 | Jang et al. |
| 5,755,734 | A | 5/1998 | Richter et al. |
| 5,755,735 | A | 5/1998 | Richter et al. |
| 5,755,770 | A | 5/1998 | Ravenscroft |
| 5,755,771 | A | 5/1998 | Penn et al. |
| 5,755,778 | A | 5/1998 | Kleshinski |
| 5,762,631 | A | 6/1998 | Klein |
| 5,776,101 | A | 7/1998 | Goy |
| 5,776,161 | A | 7/1998 | Globerman |

(56) References Cited

U.S. PATENT DOCUMENTS

| | | |
|---|---|---|
| 5,776,180 A | 7/1998 | Goicoechea et al. |
| 5,782,906 A | 7/1998 | Marshall et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane et al. |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,015,431 A | 1/2000 | Thornton et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,073 A | 8/2000 | Webster et al. |
| 6,099,497 A | 8/2000 | Adams et al. |
| 6,102,938 A | 8/2000 | Evans et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,146,356 A | 11/2000 | Wang et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,353 B1 | 2/2001 | Makower et al. |
| 6,190,403 B1 | 2/2001 | Fischell et al. |
| 6,193,746 B1 | 2/2001 | Strecker |
| 6,203,568 B1 | 3/2001 | Lombardi et al. |
| 6,203,569 B1 | 3/2001 | Wijay |
| 6,210,380 B1 | 4/2001 | Mauch |
| 6,210,429 B1 | 4/2001 | Vardi et al. |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,251,133 B1 | 6/2001 | Richter et al. |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Ehr et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,371,978 B1 | 4/2002 | Wilson |
| 6,383,213 B2 | 5/2002 | Wilson et al. |
| 6,383,215 B2 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,567 B2 | 8/2002 | Wilson et al. |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,468,302 B2 | 10/2002 | Cox et al. |
| 6,475,208 B2 | 11/2002 | Mauch |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,508,836 B2 | 1/2003 | Wilson et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigus et al. |

(56) References Cited

U.S. PATENT DOCUMENTS

| | | | |
|---|---|---|---|
| 6,540,779 B2 | 4/2003 | Richter et al. | |
| 6,572,647 B1 | 6/2003 | Supper et al. | |
| 6,576,009 B2 | 6/2003 | Ryan et al. | |
| 6,579,309 B1 | 6/2003 | Loos et al. | |
| 6,579,312 B2 | 6/2003 | Wilson et al. | |
| 6,582,394 B1 | 6/2003 | Reiss et al. | |
| 6,582,459 B1 | 6/2003 | Lau et al. | |
| 6,596,020 B2 | 7/2003 | Vardi et al. | |
| 6,596,022 B2 | 7/2003 | Lau et al. | |
| 6,599,315 B2 | 7/2003 | Wilson | |
| 6,599,316 B2 | 7/2003 | Vardi et al. | |
| 6,602,284 B2 | 8/2003 | Cox et al. | |
| 6,641,609 B2 | 11/2003 | Globerman | |
| 6,645,241 B1 | 11/2003 | Strecker | |
| 6,652,573 B2 | 11/2003 | von Oepen | |
| 6,669,717 B2 | 12/2003 | Marotta et al. | |
| 6,676,667 B2 | 1/2004 | Mareiro et al. | |
| 6,679,911 B2 | 1/2004 | Burgermeister | |
| 6,682,536 B2 | 1/2004 | Vardi et al. | |
| 6,689,156 B1 | 2/2004 | Davidson et al. | |
| 6,692,483 B2* | 2/2004 | Vardi et al. | 604/529 |
| 6,695,877 B2 | 2/2004 | Brucker et al. | |
| 6,706,062 B2 | 3/2004 | Vardi et al. | |
| 6,709,440 B2 | 3/2004 | Matin et al. | |
| 6,736,841 B2 | 5/2004 | Musbach et al. | |
| 6,770,092 B2 | 8/2004 | Richter | |
| 6,780,174 B2 | 8/2004 | Mauch | |
| 6,802,856 B2 | 10/2004 | Wilson | |
| 6,827,735 B2 | 12/2004 | Greenberg | |
| 6,827,736 B2 | 12/2004 | Perouse | |
| 6,843,803 B2 | 1/2005 | Ryan et al. | |
| 6,852,124 B2 | 2/2005 | Cox et al. | |
| 6,855,125 B2 | 2/2005 | Shanley | |
| 6,884,258 B2 | 4/2005 | Vardi et al. | |
| 6,890,349 B2 | 5/2005 | McGuckin, Jr. et al. | |
| 6,896,699 B2 | 5/2005 | Wilson et al. | |
| 6,908,477 B2 | 6/2005 | McGuckin, Jr. et al. | |
| 6,942,689 B2 | 9/2005 | Majercak | |
| 6,955,687 B2 | 10/2005 | Richter et al. | |
| 6,955,688 B2* | 10/2005 | Wilson et al. | 623/1.35 |
| 6,962,602 B2 | 11/2005 | Vardi et al. | |
| 6,980,174 B2 | 12/2005 | Flasza et al. | |
| 7,018,400 B2 | 3/2006 | Lashinski et al. | |
| 7,056,323 B2 | 6/2006 | Mareiro et al. | |
| 7,105,019 B2 | 9/2006 | Hojeibane | |
| 7,118,593 B2 | 10/2006 | Davidson et al. | |
| 7,125,419 B2 | 10/2006 | Sequin et al. | |
| 7,163,553 B2 | 1/2007 | Limon | |
| 7,238,197 B2 | 7/2007 | Sequin et al. | |
| 7,244,853 B2 | 7/2007 | Schreiber et al. | |
| 7,252,679 B2 | 8/2007 | Fischell et al. | |
| 7,344,514 B2 | 3/2008 | Shanley | |
| 7,387,639 B2 | 6/2008 | Bourang et al. | |
| 2001/0037146 A1 | 11/2001 | Lau et al. | |
| 2001/0039448 A1 | 11/2001 | Dibie | |
| 2002/0013618 A1 | 1/2002 | Marotta et al. | |
| 2002/0032478 A1 | 3/2002 | Boekstegers et al. | |
| 2002/0058990 A1 | 5/2002 | Jang | |
| 2002/0123790 A1 | 9/2002 | White et al. | |
| 2002/0156516 A1 | 10/2002 | Vardi et al. | |
| 2002/0165604 A1 | 11/2002 | Shanley | |
| 2002/0193872 A1 | 12/2002 | Trout, III et al. | |
| 2002/0193873 A1 | 12/2002 | Brucker et al. | |
| 2003/0009209 A1 | 1/2003 | Hojelbane | |
| 2003/0009214 A1 | 1/2003 | Shanley | |
| 2003/0014102 A1 | 1/2003 | Hong et al. | |
| 2003/0114911 A1* | 6/2003 | Lupton | 623/1.11 |
| 2003/0125802 A1 | 7/2003 | Callol et al. | |
| 2003/0181923 A1 | 9/2003 | Vardi | |
| 2004/0015227 A1 | 1/2004 | Vardi et al. | |
| 2004/0049259 A1 | 3/2004 | Strecker | |
| 2004/0138737 A1 | 7/2004 | Davidson et al. | |
| 2004/0148006 A1 | 7/2004 | Davidson et al. | |
| 2005/0015108 A1 | 1/2005 | Williams et al. | |
| 2005/0075722 A1 | 4/2005 | Chuter | |
| 2005/0209673 A1 | 9/2005 | Shaked | |
| 2005/0245941 A1 | 11/2005 | Vardi et al. | |
| 2007/0112407 A1* | 5/2007 | Mertens et al. | 623/1.11 |
| 2007/0179591 A1 | 8/2007 | Baker et al. | |
| 2007/0288082 A1* | 12/2007 | Williams | 623/1.11 |
| 2008/0255581 A1 | 10/2008 | Bourang et al. | |

FOREIGN PATENT DOCUMENTS

| | | |
|---|---|---|
| DE | 9014845.2 | 9/1991 |
| DE | 29701758 | 5/1997 |
| DE | 60036233 | 5/2008 |
| EP | 0891751 | 1/1999 |
| EP | 0897700 | 2/1999 |
| EP | 0904745 | 3/1999 |
| EP | 1031328 | 8/2000 |
| EP | 0884028 | 2/2002 |
| EP | 0646365 | 1/2004 |
| EP | 0684022 | 2/2004 |
| EP | 0897698 | 6/2004 |
| EP | 1182989 | 12/2004 |
| EP | 1 512 380 A1 | 3/2005 |
| EP | 0551179 | 4/2005 |
| EP | 1157674 | 7/2005 |
| EP | 0804907 | 11/2005 |
| EP | 1031330 | 11/2005 |
| EP | 0876805 | 8/2006 |
| FR | 2678508 | 1/1993 |
| JP | 8-299456 | 11/1996 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 95/08965 | 4/1995 |
| WO | WO 95/21592 | 8/1995 |
| WO | WO 96/29955 | 10/1996 |
| WO | WO 96/34580 | 11/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41802 | 11/1997 |
| WO | WO 97/45073 | 12/1997 |
| WO | WO 98/17204 | 4/1998 |
| WO | 9819628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/00835 | 1/1999 |
| WO | WO 99/15103 | 4/1999 |
| WO | WO 99/17680 | 4/1999 |
| WO | WO 99/34749 | 7/1999 |
| WO | WO 99/35979 | 7/1999 |
| WO | WO 99/36002 | 7/1999 |
| WO | WO 99/39661 | 8/1999 |
| WO | WO 99/49793 | 10/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |
| WO | WO 2004/026180 | 4/2004 |
| WO | WO 2005/107643 | 11/2005 |
| WO | WO 2005107643 A1 * | 11/2005 ............ A61F 2/06 |

(56) References Cited

FOREIGN PATENT DOCUMENTS

| WO | WO 2006/033126 | 3/2006 |
|---|---|---|
| WO | WO 2006/124162 | 11/2006 |
| WO | WO 2007/100672 | 9/2007 |

OTHER PUBLICATIONS

Carrie et al., ""T"—Shaped Stent Placement: A Technique for the Treatment of Dissected Bifurcation Lesions," Catheterization and Cardiovascular Diagnosis, vol. 37, pp. 311-313, 1996.
Chevalier et al., "Placement of Coronary Stents in Bifurcation Lesions by the "Culotte" Technique," The American Journal of Cardiology, vol. 82, pp. 943-949, Oct. 15, 1998.
Colombo et al., ""Kissing" Stents for Bifurcational Coronary Lesion," Catheterization and Cardiovascular Diagnosis, vol. 30, pp. 327-330, 1993.
U.S. Appl. No. 08/642,297, filed May 3, 1996, to Richter et al.
U.S. Appl. No. 09/325,996, filed Jun. 4, 1999, to Vardi et al.
U.S. Appl. No. 09/533,616, filed Mar. 22, 2000, to Vardi et al.
U.S. Appl. No. 09/614,472, filed Jul. 11, 2000, to Davidson et al.
U.S. Appl. No. 09/663,111, filed Sep. 15, 2000, to Davidson et al.
Dichek et al., "Seeding of Intravascular Stents with Genetically Engineered Endothelial Cells," Circulation, vol. 80, No. 5, pp. 1347-1353, Nov. 1989.
Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.
Katoh et al., "New Double Wire Technique to Stent Ostial Lesions," Catheterization and Cardiovascular Diagnosis, vol. 40, pp. 400-402, 1997.
Lear et al., "The Northridge Earthquake as a Trigger for Acute Myocardial Infarction," 1 page, 1996.
Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.
Nakamura et al., "Techniques for Palmaz-Schatz Stent Deployment in Lesions with a Large Side Branch," Catheterization and Cardiovascular Diagnosis, vol. 34, pp. 353-361, 1995.
Satler et al. "Bifurcation Disease: To Treat or Not to Treat," Catheterization and Cardiovascular Interventions, vol. 50, pp. 411-412, 2000.
SCIMED Life Systems, Inc., "TRIO 14 PTCA Catheter, Re-Engineering Over-The-Wire Balloon Technology," Brochure, 4 pages, 1994.
Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.
Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

* cited by examiner

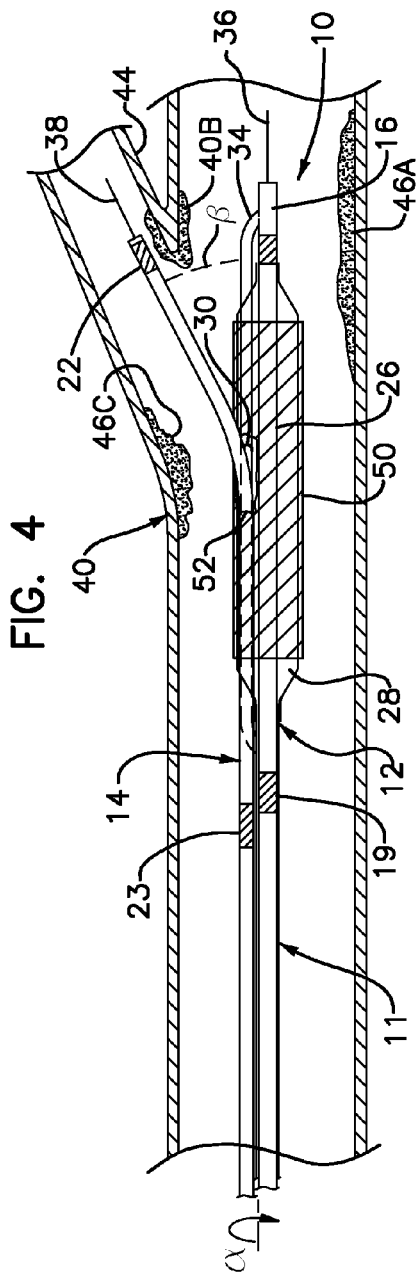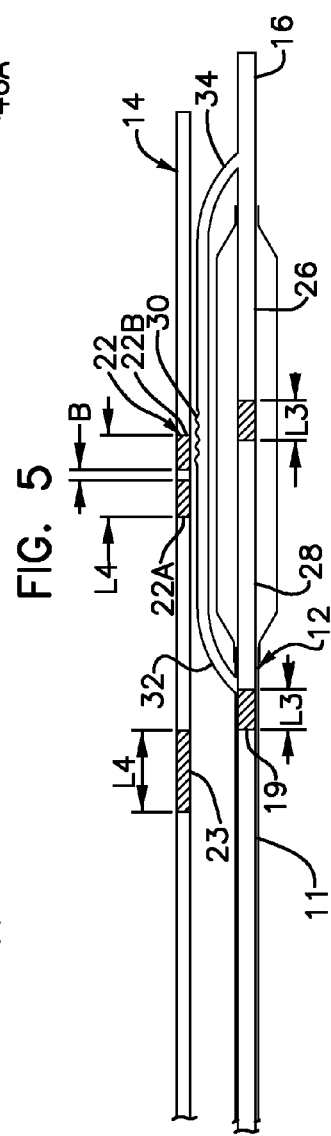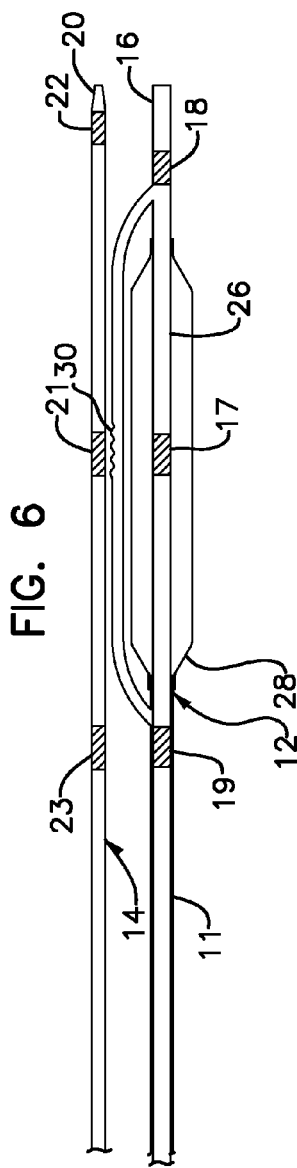

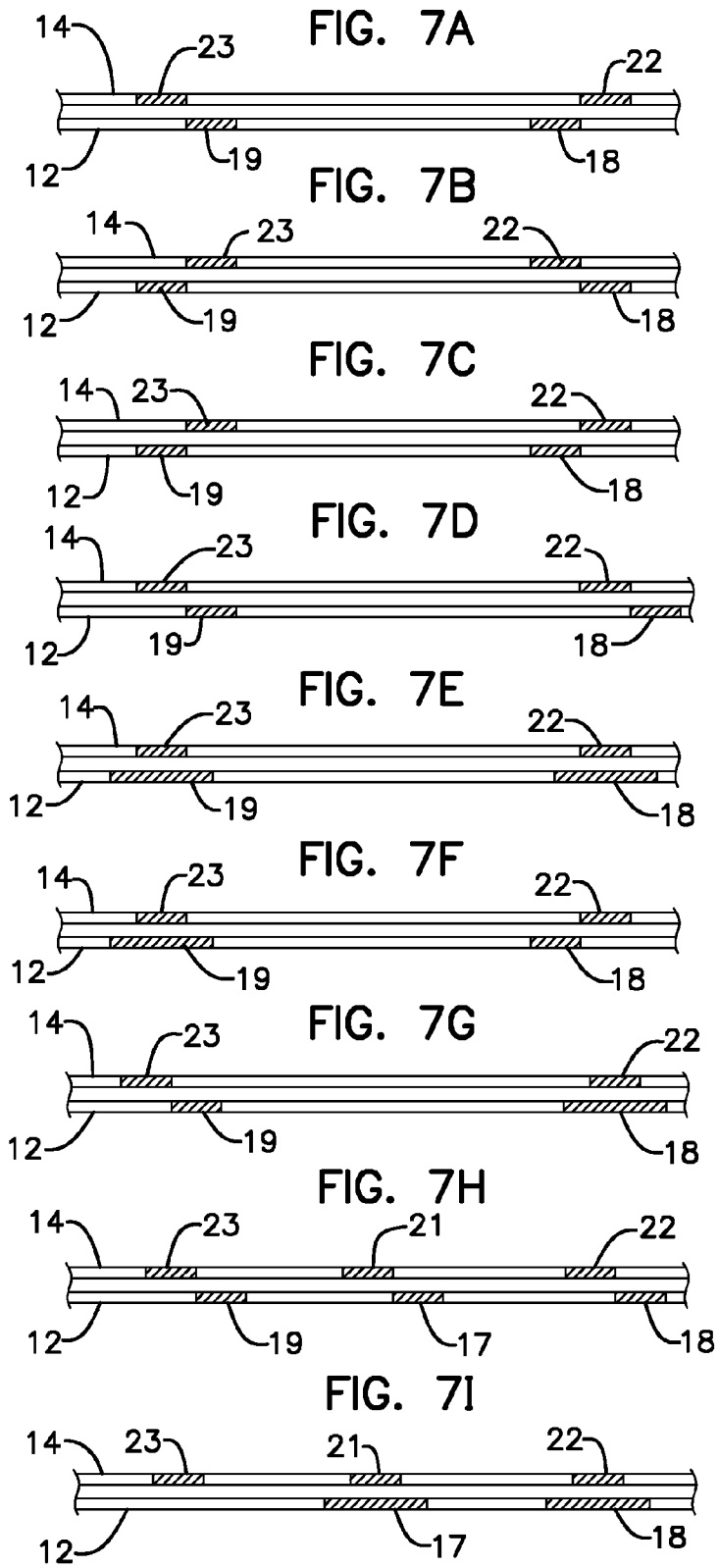

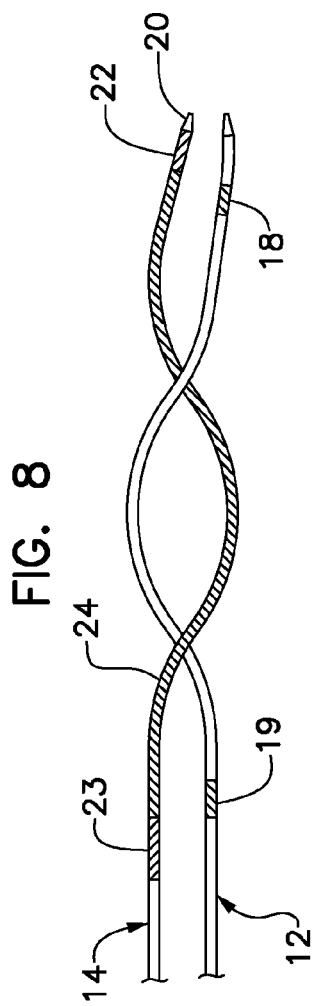
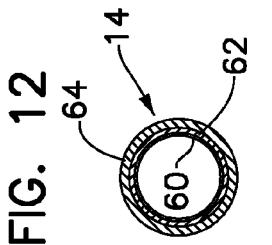
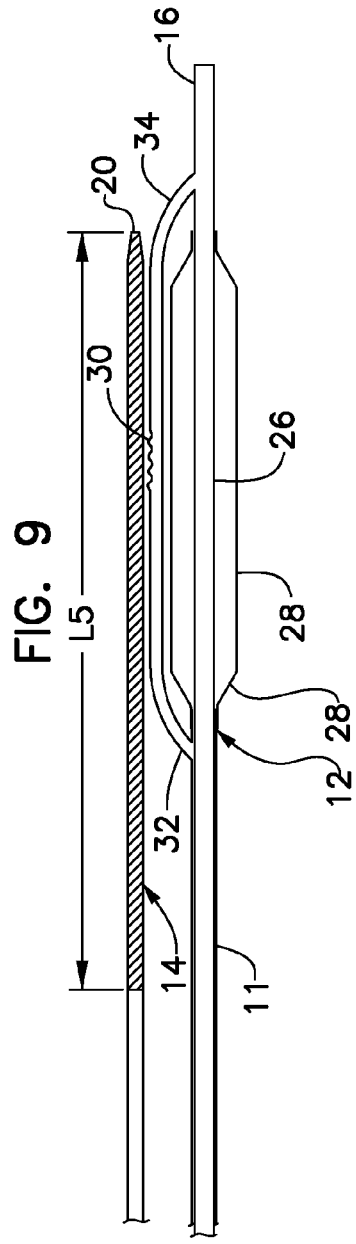
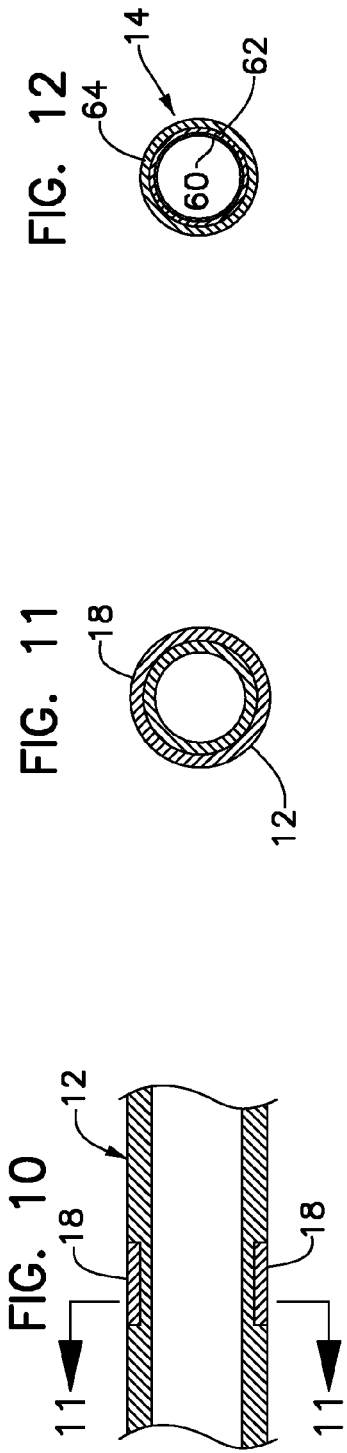

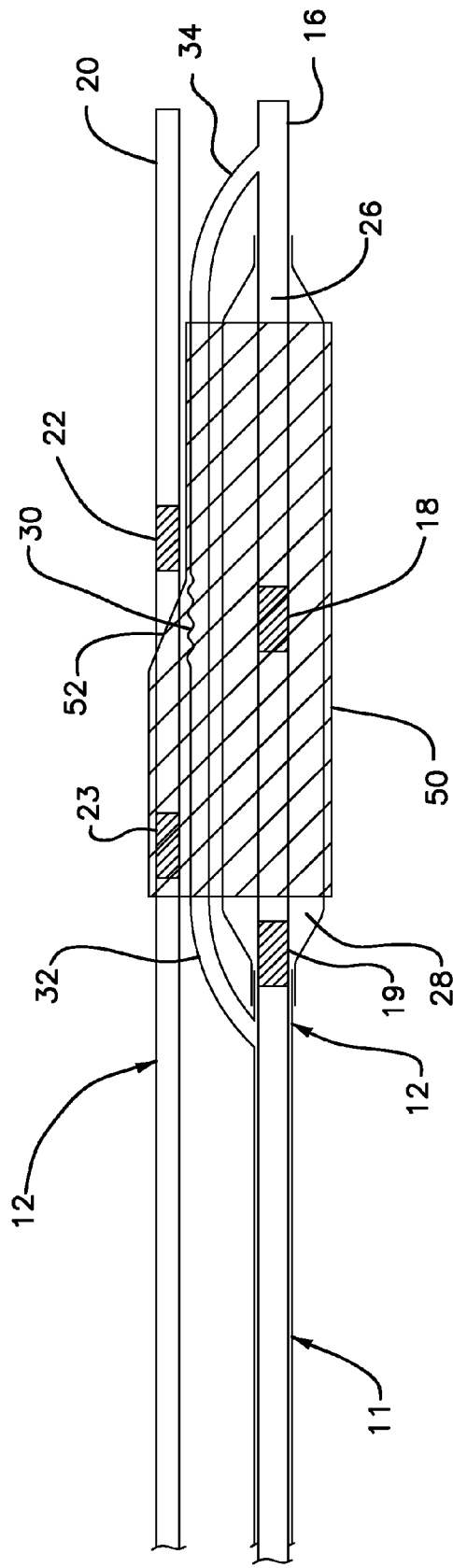

MARKER ARRANGEMENT FOR BIFURCATION CATHETER

CROSS REFERENCE TO RELATED APPLICATIONS

This application claims priority to U.S. Provisional Application No. 60/776,149 filed on Feb. 22, 2006, entitled MARKER ARRANGEMENT FOR BIFURCATION CATHETER, the disclosure of which is incorporated by reference herein in its entirety.

TECHNICAL FIELD

This disclosure relates to catheter assemblies configured for use with multiple guidewires. Preferred arrangements provide for catheters assemblies with marker arrangements that are useful in visually aligning features of the catheter assembly and methods related to the same.

BACKGROUND

Catheters are used with stents and balloon inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall and treating dissections in blood vessel walls caused by balloon angioplasty of coronary arteries.

While conventional stent technology is relatively well developed, stent technologies related to treatment of the region of a vessel bifurcation are still being developed. One challenge related to treatment of a vessel bifurcation involves alignment of the stent relative to the vessel branches of the vessel bifurcation.

SUMMARY OF THE DISCLOSURE

The present disclosure relates to catheter assemblies having first and second catheter branches or shafts that are configured for advancement over separate guidewires to a treatment site within a patient. A given catheter assembly includes a marker configuration wherein each catheter branch can include a plurality of markers. A comparison of the position and arrangement of markers on one catheter branch relative to the position and arrangement of markers on the other catheter branch can provide a visual indication of axial and radial positioning of catheter branches relative to each other. Differences in the marker arrangements, including size, shape, and axially positioning on the catheter branches can also be helpful in visually distinguishing one catheter branch from the other.

The markers on the main and side catheter branches can be arranged in any of a plurality of arrangements that result in different marker configurations for the catheter assembly. In one example, the markers on the side catheter branch are spaced apart axially a distance greater than a spacing between the markers of the main catheter branch, and the markers of the main catheter branch are positioned at a location axially between the markers of the side catheter branch. In another example, the markers on the side catheter branch are spaced apart a distance wherein a proximal marker is spaced proximal of a proximal end of a stent carried by the catheter assembly, and a distal marker is positioned distal of the side opening of the stent. In a further example, the side catheter branch markers are spaced apart a distance at least as great as a length of the stent. The markers of the stent delivery system can also be imageably distinct from each other as a result of, for example, different markers sizes, shapes and materials.

Another aspect of the present disclosure relates to the addition of an elongate marker member to at least one of the side and main catheter branches. The elongate marker member can include a coil structure, such as a helical shaped coil, that extends along a portion of the catheter branch length. The elongate marker member can also be configured as, for example, a braid, a series of connected rings, or other structure having a shape that is non-linear relative to an axis of the catheter branch. The marker member can also be defined as part of the catheter branch material composition. The length of the elongate marker member is typically at least twice as long as common radiopaque markers used with bifurcation stent delivery systems.

There is no requirement that an arrangement include all features characterized herein to obtain some advantage according to this disclosure.

BRIEF DESCRIPTION OF THE DRAWINGS

FIG. 4 is a schematic side view of the stent deliver system shown in FIG. 4 with the side catheter branch rotated out of alignment relative to the side opening of the branch vessel.

FIG. 5 is a schematic side view of some alternative marker arrangements in accordance with principles of the present disclosure.

FIG. 6 is a schematic side view of some further alternative marker arrangements in accordance with principles of the present disclosure.

FIGS. 7A-I schematically illustrate a variety of example marker arrangements in accordance with principles of the present disclosure.

FIG. 8 is a schematic side view of some example catheter branches of a stent delivery system in a twisted arrangement.

FIG. 9 is a schematic side view of portions of a stent delivery system wherein a portion of the side catheter branch includes radiopaque material.

FIG. 10 is a schematic cross-sectional view of a catheter branch of a stent delivery system having an encapsulated marker member.

FIG. 11 is a schematic cross-sectional view of a catheter branch of a stent delivery system taken along indicators 11-11 in FIG. 10.

FIG. 12 is a schematic cross-sectional view of another example catheter assembly having an alternative marker arrangement relative to the stent.

FIG. 13 is a schematic side view of some additional alternative marker arrangements in accordance with principles of the present disclosure.

DETAILED DESCRIPTION

General Background

Figure 1:
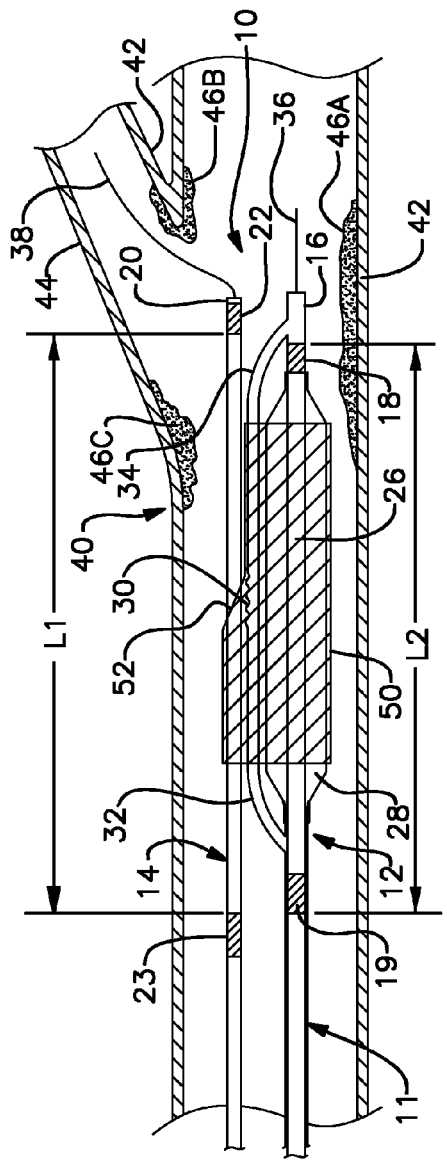
FIG. 1 is a schematic side view of a stent delivery system constructed according to principles of this disclosure and positioned adjacent a vessel bifurcation.

This disclosure relates to catheter assemblies configured for use with multiple guidewires. Marker bands and other marker features can be used to visually identify the various catheter branches and the relative position of the catheter branches, for example, during treatment of a vessel bifurcation. The disclosed catheter assemblies and related methods include a main catheter branch and a side catheter branch. A main balloon is typically positioned at a distal end portion of the main catheter branch. When using the catheter assemblies for delivery of a stent, the stent is also positioned on the main balloon at the distal end portion of the main catheter branch. The side catheter branch can be used to help orient the stent relative to a branch vessel at a vessel bifurcation.

Bifurcation stent delivery systems are particularly useful for treating vessel bifurcations. A bifurcation stent is typically configured to provide access through a side opening of the stent into a branch vessel of the vessel bifurcation. In some embodiments, the stent also includes extension structure that extends radially outward from the stent to at least partially into the branch vessel.

The use of multiple guidewires simultaneously within a common lumen such as a blood vessel can result in cross-over of the guidewires along their lengths and cross-over of the catheter branches that move over the guidewires. When one guidewire is directed into a branch vessel and another guidewire is maintained in the main vessel of a vessel bifurcation, cross-over or relative rotation of the catheter branches passing over those guidewires can result in misalignment of the stent relative to the opening of the branch vessel.

In some applications, such as in bifurcation stent delivery systems, features of the stent (e.g., the side opening) must be axially aligned, radially aligned, or both axially and radially aligned relative to an opening into or ostium of the branch vessel of the vessel bifurcation. If the catheter branches are rotated relative to each other, misalignment of the stent features is likely to result, thereby causing deployment of the stent at an orientation that does not provide most effective treatment of the vessel bifurcation. Identification of relative rotation between and the relative axial and radial position of the catheter branches using the example marker systems described below can provide the system operator with an understanding of the relative position of the catheter branches so that adjustments can be made prior to deploying the stent at the vessel bifurcation. In many cases, the mere distinguishing between the main and side catheter branches can result in improved treatment and correction by the operator.

The Embodiment of FIGS. 1-4

An illustrated view of one embodiment of a stent delivery system 10 is shown with reference to FIGS. 1-4. Stent delivery system 10 includes a catheter shaft 11, a main catheter branch 12 and a side catheter branch 14. The main catheter branch 12 is configured to advance over a main guidewire 36. The main catheter 12 includes a distal tip 16 and at least first and second markers 18, 19. The markers 18, 19 are axially spaced apart a length L1 along the main catheter branch 12. The side catheter branch 14 defines a side branch lumen ("SBL") that is sized to advance over a branch guidewire 38. The side catheter branch 14 includes a distal end 20 and at least first and second markers 22, 23. The markers 22, 23 are axially spaced apart a length L2 along the side catheter branch 14. The length L1 is shown as a minimum length measurement between the markers 18, 19. The length L2 is shown as a maximum length measurement between the markers 22, 23.

The main catheter branch 12 includes a main guidewire member 26, a main balloon 28, and a side balloon 30. The guidewire member 26 defines a main guidewire lumen sized to advance over the main guidewire 36. The side balloon 30 includes a proximal portion 32 that that intersects the main catheter branch 12 proximal of the main balloon 28, and a distal portion 34 that intersects the main guidewire member 26 distal of the main balloon 28. The side balloon 30 is configured to extend radially outward relative to the main balloon 28 when the side balloon 30 is inflated.

The main balloon 28 is configured to remain in a main vessel of a vessel bifurcation at an axial position that spans an opening into a branch vessel of the vessel bifurcation. The side balloon 30 is configured to expand into an opening of the branch vessel. The side balloon 30, when inflated, typically expands a portion of the stent structure that defines the side opening of the stent into the side open of the branch vessel.

Typically, the main and side balloons 28, 30 are coupled in fluid communication with a common inflation lumen that is defined in the catheter shaft 11. The common inflation lumen can be conventional, and extend distally from a proximal end of the stent delivery system that remains outside of the patient (not shown). The common inflation lumen is used to supply pressurized inflation fluid to the main and side balloons 28, 30 during inflation and drain the inflation fluid when deflating the balloons 28, 30.

The balloons 28, 30 are illustrated as separate balloons that are positioned adjacent to each other. In other balloon arrangements, the side balloon 30 is positioned on the main balloon 28. For example, the side balloon 30 can be integral with the main balloon 28, or be formed as a separate piece that is secured to the outer surface of the main balloon 30. The side balloon 30 can also be integrated into the side catheter branch 14 or another catheter branch of the catheter assembly, such as described in co-pending U.S. patent application Ser. No. 10/644,550, entitled STENT WITH A PROTRUDING BRANCH PORTION FOR BIFURCATING VESSELS. The side catheter branch 14 in this exemplary embodiment is exterior to and distinct from the main catheter branch 12.

In operation, the side catheter branch 14 extends through a sidewall opening 52 of the stent 50 (see FIGS. 1-3) and be directed along the guidewire 38 into a side branch vessel of a vessel bifurcation as described in more detail below. The side catheter branch 14 and stent 50 can be of the type described in, for example, U.S. Pat. No. 6,325,826 to Vardi, et al., and U.S. Published Patent Application No. 2004/0138737 to Davidson.

Figure 2:
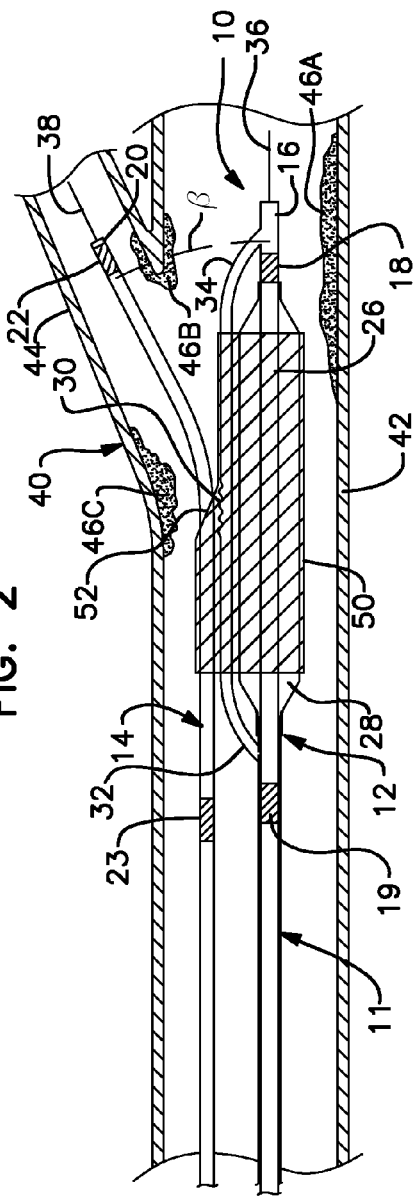
FIG. 2 is a schematic side view of the stent delivery system shown in FIG. 1 with the side catheter branch extending into a branch vessel of the vessel bifurcation.
Figure 3:
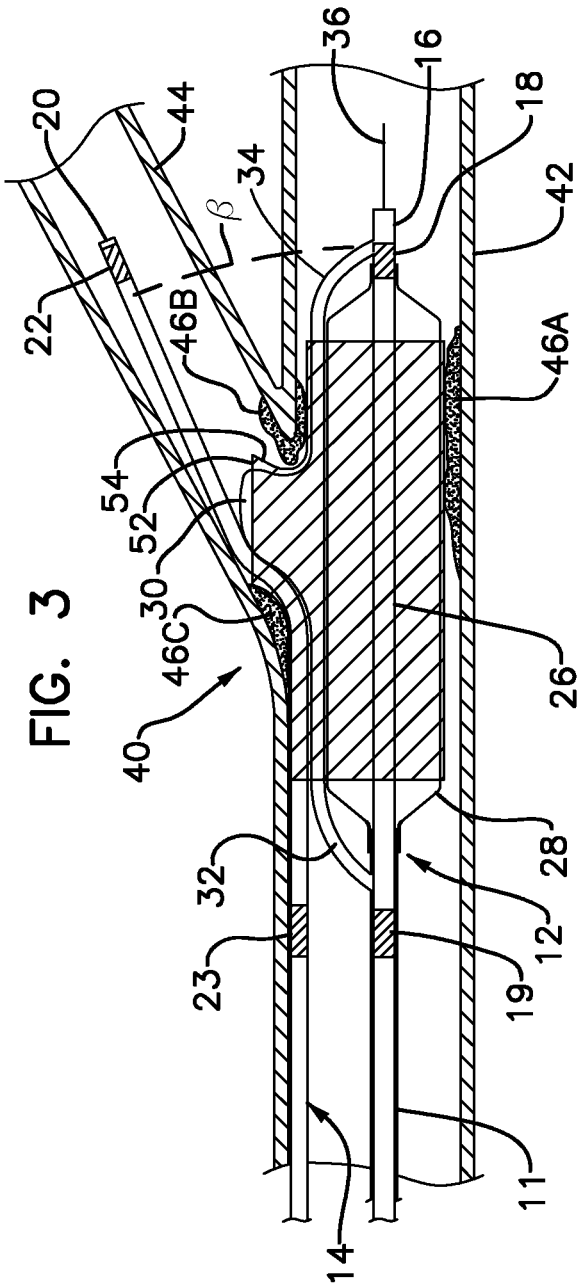
FIG. 3 is a schematic side view of the stent delivery system shown in FIG. 2 with the balloon members inflated and the stent expanded.

FIGS. 1-3 illustrate stent delivery system 10 in relation to a vessel bifurcation 40. The vessel bifurcation 40 includes a main vessel 42, a branch vessel 44, and a plurality of obstructions 46A-C. When using the stent delivery system 10 to treat the vessel bifurcation 40, the guidewires 36, 38 are navigated to the treatment site with the guidewire 36 positioned in the main vessel 42 and the guidewire 38 positioned extending from the main vessel 42 into the branch vessel 44 (see FIG. 1). The stent delivery system 10 is then advanced over the guidewires 36, 38 into position adjacent to the vessel bifurcation 40 within the main vessel 42. The stent delivery system 10 is shown in FIG. 1 with the main catheter branch 12 extending through the stent 50 and the side catheter branch 14 extending into a proximal end of the stent and out of the stent side opening 52. The side catheter branch 14 maintains a generally parallel arrangement with the main catheter branch 12 prior to being advanced to the vessel bifurcation 40. The catheter branches 12, 14 are shown in FIG. 1 extending in parallel without any cross-over or relative twisting of the branches 12, 14. Typically, the catheter branches 12, 14 are secured together at a proximal location and thus maintain a fixed axial position relative to each other.

The markers 18, 19 and 22, 23 are shown in FIG. 1 positioned on the main and side catheter branches 12, 14 with a spacing between a proximal end of marker 22 and a distal end of marker 23 (L2) that is at least as great as the spacing between a distal end of marker 18 and a proximal end of marker 19 (L1). With this arrangement, the markers 18, 19 can be positioned axially between the markers 22, 23. If one of the pairs of markers 18, 22 or 19, 23 overlap axially while the other of the pairs of markers are properly aligned end-to-end (e.g., the end-to-end arrangement of markers 18, 22 shown in FIG. 1), the operator of the stent delivery system 10 can identify cross-over or twisting of the branches 12, 14 in the area between the sets of markers 18, 22 and 19, 23. Further, if only two or three of the markers 18, 19, 22, 23 are visible at a given time due to overlap of the markers, the operator can be aware that features of the catheter branches 12, 14 are not radially aligned.

Referring now to FIG. 2, the side catheter branch 14 has been navigated further along the guidewire 38 and into the branch vessel 44. The stent 50 is properly aligned both axially and radially as confirmed by the relative offset position of the markers 18, 22 and 19, 23. The operator can visually inspect the spatial relationship between markers 18 and 22 by projecting a rotation arch β to approximate whether the relative offset positioning shown in FIG. 1 is maintained. In a case where the catheter branches have experienced twisting or cross-over such as shown in FIG. 4, the incorrect relative spacing between markers 18, 22 along the projected arch β shows that the distal end of marker 22 is proximal of the proximal end of marker 18.

In some cases it may be difficult for the operator to visually determine the relative alignment of markers 18, 22 in the case of steep angles β or extensive distance of the marker 22 from the stent sidewall opening 52. In such cases, it may be beneficial to provide additional markers or other types of features on one or both of the catheter branches 12, 14. The addition of extra markers can improve visualization of the positioning of the catheter branches relative to each other. Alternative marker arrangements and marker features are described in further detail below with reference to FIGS. 5-12.

FIG. 4 illustrates twisting of the side catheter branch 14 relative to the main catheter branch 12 along a length of the side catheter branch 14 from the stent opening 52 to the distal tip 20 of the side catheter branch 14. The opening 52 along with the bifurcated balloon 26 and that portion of the catheter branch 14 in the proximal end of the stent 50 are rotated about a longitudinal axis of the main catheter branch 12 an angel α of about 70 to about 80 degrees out of a plane that extends parallel with the longitudinal axis of the main and branch vessels 42, 44 of the vessel bifurcation 40. While the markers 19, 23 are in proper axially offset orientation with both markers visible, the distal end of marker 23 abutting proximal end of marker 19, and marker 23 vertically above marker 19 (in this view), the twist towards the distal end of catheter branch 14 results in the proximal end of marker 22 being positioned proximal of the proximal end of marker 18 (via projection through angle β). The operator can infer from this arrangement of markers 18, 22 and 19, 23 that the stent opening 52 is not radially aligned with the opening in the branch vessel 44.

After the stent delivery system has been positioned as shown in FIG. 1, the markers 18, 19 and 22, 23 are used to determine whether cross-over or twisting of the catheter branches 12, 14 is present along the length of the branches between the pairs of markers 18, 19 and 22, 23. The distal tip 20 of the side catheter branch 14 is navigated into the branch vessel 44 a distance sufficient to illustrate an angle β of separation that indicates the branch 14 is within the branch vessel 44. Sometimes the angle β is relatively small when the angle at which the branch vessel 44 extends from the main vessel 42 is large (e.g., greater than 45 degrees). However, when the branch vessel 44 extends from the main vessel 42 at a relatively small angle (e.g., less than 45 degrees), it may be necessary to insert the catheter branch 14 further into the branch vessel to obtain a visual confirmation that the catheter branch 14 is actually in the branch vessel. Typically, the greater the angle β the more difficult it becomes to visualize the relative axial position of the markers 18, 22.

Once the stent delivery system 10 is positioned with the sidewall opening 52 and auxiliary inflatable portion 34 aligned with the opening into the branch vessel 44, pressurized fluid is supplied to the main and auxiliary inflatable portions 32, 34 to dilate and expand stent 50 (see FIG. 3). The main inflatable portion 32 primarily expands a main body portion of the stent. The auxiliary inflatable portion 34 expands the sidewall opening 52 and an extendable structure 54 of the stent 50 that extends radially away from the main body portion of the stent and into the branch vessel 44. After the inflatable portions 32, 34 have been inflated and the stent expanded, the bifurcated balloon 26 is deflated by draining the inflation fluid out of the main catheter branch 12. This allows the inflatable portions 32, 34 to collapse in preparation for withdrawal of the main and side catheter branches 12, 14 from the vessel bifurcation 40.

The extendable structure 54 of the stent 50 can have a variety of configurations such as those configurations disclosed in co-pending U.S. Published Patent Application Nos. 2004/0138737 and 2005/0015108, which patent applications are incorporated herein by reference.

Alternative Marker Configurations

FIG. 5 illustrates an alternative marker configuration in which the markers are imageably distinct from each other. Imageably distinct can be defined in the context of viewing a catheter marker inside a body lumen as being viewable by an imaging system, such as those imaging systems commonly used to view stent delivery procedures. An example imaging system is a C-arm radiographic device that images a vessel using fluoroscopy and provides images of the vessel and in-situ stent delivery features on a screen. The structure and composition of the markers can influence the ability of a viewer to distinguish between markers. For example, the length of the marker is one structural difference that can provide image distinction. The diameter, cross-sectional shape and material thickness of the markers are other example structural differences that provide image distinction. The type and concentration of radiopaque material in the markers are example composition differences that provide image distinction. The relative location of the markers at different positions on the main and side catheter branches 12, 14 as compared to the embodiment shown in FIGS. 1-4, alone or in combination with structural and composition difference between markers can also be useful.

The markers 18 and 19 shown in FIG. 5 each have an equal length L3 whereas the markers 22, 23 have lengths L4 that are different from the length L3. In one example, the length L4 is about 20% to about 200% of the value of L3, more preferably about 25% to about 175% of the value of L3, and most preferably about 25% to about 50% greater or about 25% to about 50% smaller than the value of L3. Thus, the length L3 of markers 18 and 19 can be made greater or smaller than the length L4 of the markers 22, 23 within, for example, the preferred ranges described above.

The total length of each of markers 18, 19, 22, 23 is typically in the range of about 0.5 mm to about 5 millimeters long, more preferably about 0.75 mm to about 2 millimeters long, and most preferably about 0.75 mm to about 1 millimeter long. The material composition of the markers is a consideration for the marker length, the marker material thickness, and the cross-sectional size of the markers. Typically, the materials used for the markers have a greater stiffness than the stiffness of the material of the catheter branches 12, 14 to which the markers are mounted. The use of most markers, regardless of the size and shape, can reduce to some degree the flexibility of the catheter branches to which the markers are mounted. Shortening the length of the markers can minimize negative effects on catheter flexibility. Markers that are too short can become difficult to visualize. Optimizing the size and shape of the markers to provide adequate visualization while minimizing added stiffness in the catheter is one objection of the markers and marker arrangements disclosed herein.

One option for providing the appearance of one longer marker is to position two shorter markers adjacent to each other with a small gap there between. FIG. 5 illustrates marker 22 comprising segments 22A and 22B that are spaced apart axially a distance B. Typically, the distance B would be made small enough that the break between segments 22A and 22B is not perceptible, while still providing some relative movement between the segments that leads to the addition of minimum stiffness to the catheter branch 14.

The markers 18, 19, 22, 23 can comprise different material compositions that provide differing amounts of visualization of the marker, stiffness, ease of handling and forming of the marker, and other considerations. Some example materials used in the markers include platinum, tantalum, and gold plated steel. The markers usually comprise materials that are generally categorized as radiopaque materials that obstruct the transmission of radiant energy, such as the energy emitted from a C-arm radiographic device.

In the arrangement of FIG. 5, the marker 18 is positioned on the main catheter branch 12 in axial alignment with the side balloon 30. This position of marker 18 can help the operator visually align the side balloon 30 more accurately with an opening into a branch vessel of a vessel bifurcation. The markers 22, 23 are spaced apart axially a distance substantially equal to a spacing between the markers 18, 19. As a result, the markers 22, 23 can be positioned just proximal of the markers 18, 19 as shown in FIG. 5 to provide a parallelogram-type arrangement among the markers 18, 19, 22, 23, wherein lines drawn between markers 18, 22, between markers 22, 23, between markers 23, 19, and between markers 19, 18 provides a parallelogram structure having two pairs of parallel lines.

FIG. 6 illustrates another marker arrangement that includes a third marker 17 positioned on the main catheter branch 12 at a location between the markers 18, 19, and a third marker 21 positioned on the side catheter branch 14 at a location between the markers 22, 23. Branch 12 includes markers 18, 17, 19 that are positioned at distal, center, and proximal locations, respectively, relative to the bifurcated balloon 26. The branch 14 includes markers 22, 21, 23 arranged adjacent to markers 22, 21, 23, respectively. The markers 22, 23 are spaced apart a distance sufficient for the distal end of marker 18 and the proximal end of marker 19 to be arranged axially between proximal and distal end of markers 22 and 23, respectively. When the markers 18, 19 are arranged between the markers 22, 23 the marker 21 is axially aligned with marker 17. Other embodiments may include any combination of numbers and positions for the markers relative to other markers on the same catheter branch or relative to markers on the adjacent catheter branch. For example, the six marker arrangement shown in FIG. 6 can be modified so that the distal end of each of markers 21, 22, 23 are positioned proximal of the proximal end of markers 17, 18, 19, respectively.

FIGS. 7A-I illustrate a few different marker arrangements that include two or three markers positioned on each of the catheter branches 12, 14. The markers 17, 18, 19, 21, 22, 23 can have the same or different lengths and sizes. The markers 17, 18, 19, 21, 22, 23 can be arranged in axial alignment with each other or be at least partially offset axially from each other. The number of markers on each catheter branch can be equal or unequal. The markers 17, 18, 19, 21, 22, 23 can be positioned at various locations along the catheter branches 12, 14 relative to a stent (e.g., stent 50 shown in FIG. 1) positioned on the catheter branches 12, 14 (e.g., positioned within, overlapping, or outside of the stent). For example, catheter assembly 200 shown in FIG. 13 illustrates the markers 18, 23 positioned inside the stent 50 and the markers 19, 20 outside of the stent. The markers 17, 18, 19, 21, 22, 23 can be positioned on other portions of a catheter assembly such as a main or side balloon member (e.g., portions 28, 30 of the side balloon 30 shown in FIG. 1), a guidewire member that defines a guidewire lumen, or a primary catheter shaft that defines an inflation lumen of the catheter assembly. Typically, the branches 12, 14 maintain a fixed axial relationship relative to each other prior to and during insertion of the catheter assembly into a patient.

Many other variations of the marker arrangements to create any of a number of marker arrangement shapes are possible. For example, in addition to parallelogram shapes, rectangle, rhombus, rhomboid, triangle, trapezoid, and various quadrilaterals shapes are possible marker arrangement shapes.

The markers 18, 19, 22, 23 can be configured as marker bands having a circular cross-section. The markers can also have a semi-circular, oval, or semi-oval cross-section. The markers should have sufficient circumferential shape to be mounted and then stay retained in position when secured to the catheter branch. The markers can be secured to the catheter branches in a variety of ways. For example, the markers can be secured to an outer or inner surface of the catheter branch, or embedded in or otherwise integrated within the sidewall structure of the catheter branch. FIGS. 10 and 11 illustrate swage mounting of a marker band 18 to a catheter branch 12. A swage mounting provides for the outer facing surface of the marker to be flush mounted with the outer surface of the catheter branch. Preferably, swaging a marker band onto a catheter branch does not create a decreased internal dimension of the catheter branch. Other types of mounting methods and configurations may be used for the markers include, for example, crimping, co-molding, and depositing techniques.

The axial spacing between pairs of proximal markers (e.g., markers 19, 23) and distal markers (e.g., markers 18, 22) is another variable that can be adjusted. The axial spacing between the distal ends of markers 22, 23 and the proximal ends of markers 18, 19 in FIG. 5 is substantially zero distance, which results in an end-abutting arrangement. Other embodiments can include spacing up to a length equal to two or three times the length of one of the markers being axially spaced apart. For example, in an embodiment wherein the length of marker 19 is about 1 mm and the length of marker 23 is about 1.5 mm, the spacing between the distal end of marker 23 and the proximal end of marker 19 is in the range of about 0 mm to about 3 mm (e.g., about three times the length of marker 19). Preferably, the spacing between the distal end of a marker on one catheter branch (e.g., a distal-most marker) and the proximal end of a corresponding marker on a separate catheter branch (e.g., a corresponding distal-most marker) is about 0 mm to about 3 mm, and more preferably about 0 mm to about 2 mm. While the size and shape of the markers can influence the general visibility of the markers themselves, the ability to visually assess the relative axial spacing between markers on separate catheter branches is typically not significantly influenced by the size and shape of the markers. The further the relative axial spacing between corresponding markers on separate catheter branches becomes, the more difficult it is to accurately assess whether that relative axial spacing is maintained during operation of a stent delivery system that includes the markers.

Referring now to FIG. 8, catheter branches 12, 14 are shown in a 360° symmetrical twisted relationship relative to each other. This symmetric twisted relationship between branches 12, 14 illustrates how a twist may be difficult to identify in some situations. The spacing between markers 18, 22 and between markers 19, 23 is the same as when the catheter branches are not twisted or crossed over (e.g., the spacing shown in FIG. 1). However, in the twisted configuration shown in FIG. 6, the markers 18, 22 are not the same axial distance from the markers 19, 23, respectively, due to the twisted arrangement. Further, in the case wherein markers 18, 19, 22, 23 each have the same shape, size, and material composition, it is difficult to distinguish between the catheter branches 12, 14.

In order to more clearly distinguish the catheter branch 14, the branch 14 can include a helical coil 24 extending along a portion of a length of the branch 14. The helical coil comprises a visible material such as the radiopaque material described above for use with markers 18, 19, 22, 23. The helical coil 24 extends from the marker 22 to the marker 23. The helical coil can also have different lengths and extend over different portions of the branch 14. For example, the helical coil can have an axial length at least as great as an axial length of the stent being deployed using the catheter branches 12, 14. The helical coil can be positioned on the catheter branch so that it overlaps axially with the stent. In another example, the coil extends axially from near a distal tip of the catheter branch 14 to a proximal end of the stent. For these and other examples, it is assumed that the branch 14 is secured or otherwise fixed axially relative to the main catheter branch 12 at a location proximal of the side opening in the stent through which the side catheter branch 14 extends.

The helical coil 24 can be used in combination with one or more markers on a given catheter branch. The helical coil 24 can also be used by itself on a catheter branch without any other markers on that catheter branch. The helical coil can provide visualization of the catheter branch for at least the purpose of distinguishing the catheter branches 12, 14 from each other. The helical coil can also be useful for positioning the catheter branch to which it is mounted relative to other features of a stent delivery system and vessel bifurcation.

The helical coil 24 can provide certain advantages due to the helical structure. A helical coil can provide for flexibility in a lateral direction relative to an axis of the catheter branch so that the catheter branch maintains its ability to navigate through a vessel to a vessel treatment sight. A helical coil can also be easily mounted to an outer surface of a cylindrical member such as the main and side catheter branches 12, 14. A helical coil can be embedded in a catheter branch using methods such as, for example, co-molding or extrusion techniques.

Other structures can be used in place of the helical coil 24 and provide similar advantages. For example, a braid structure, a plurality interconnected rings, or a thin layer or film can provide at least some of the same advantages and function of a helical coil. Referring to FIG. 12, one construction for mounting a helical coil 24 or other marker structure to a catheter branch is shown. FIG. 9 illustrates an inner layer 60 over which a marker layer 62 (e.g., helical coil) can be applied to an outer circumference thereof. In order to provide a smooth outer surface for the catheter branch, an outer layer 64 can be added to encapsulate the marker layer 62.

Referring to FIG. 9, another configuration is shown that addresses some of the issues described above related to distinguishing between a main and side catheter branch of a stent delivery system. Side catheter branch 14 shown in FIG. 8 comprises a marker material that is part of the material composition of the catheter branch 14. The catheter branch material can comprise, for example, a polymeric material extruded or otherwise formed into a lumen shape and comprise a radiopaque material such as platinum or tantalum. This material composition for the catheter branch 14 can be in any portion along the length of the side catheter branch 14, such as along the length L5 shown in FIG. 8. The concentration of radiopaque material in the catheter branch composition can vary to alter the visibility of the catheter branch. The length L5 of the marker material can vary. The location of the proximal and distal relative to a distal tip of the side catheter branch 14 can also vary. In one example, wherein a stent is carried by the main catheter branch 12 and the side catheter branch 14 extends through a side opening in the stent, the length L5 is at least as great as a distance between the side opening of the stent and a distal open end of the stent.

In many embodiments, the distal tips 16, 20 of the catheter branches 12, 14 include some type of marker or marker material composition. Marking the distal tip of a catheter branch can help with determining a relative position of the catheter branch relative to other features of a stent delivery system and features of the vessel through which the catheter branch travels. In one example, a marked distal tip 20 of a side catheter branch 14 can help in determining that the branch 14 has entered the vessel branch of a vessel bifurcation. By providing a length of a catheter branch (e.g., L5) with a marker material that provides visualization along that length, it may be easier to identify cross-over and twisting of the catheter branches 12, 14 relative to each other.

Materials and Other Considerations

The example systems disclosed herein may be used in over-the-wire or rapid exchange systems. Some example rapid exchanges systems are disclosed in U.S. Published Patent Application No. 2003/0181923 to Vardi et al., which application is incorporated herein by reference.

The materials used in the balloons, catheter shafts, and other components of the catheter assemblies disclosed herein can be made of any suitable material including, for example, thermoplastic polymers, polyethylene (high density, low density, intermediate density, linear low density), various copolymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 1F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the example catheter assemblies described above, the branch balloon can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in, for example, in U.S. Pat. Nos. 6,210,429 and 6,325,826 to Vardi et al., and co-pending U.S. patent application Ser. No. 10/644,550, filed on Aug. 21, 2003, and titled "Stent With a Protruding Branch Portion For Bifurcated Vessels," the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

Conclusion

One aspect of the present disclosure relates to a catheter assembly that includes a first catheter branch, a second catheter branch, first distal and proximal markers, and second distal and proximal markers. The first catheter branch includes a distal end portion that extends in a first direction. The second catheter branch includes a distal end portion that extends in a second direction that is generally the same direction as the first direction. The first distal marker and the first proximal marker are positioned on the first catheter branch. The second distal marker and the second proximal marker are positioned on the second catheter branch. The first distal marker, the first proximal marker, the second distal marker and the second proximal marker each include a distal portion and a proximal portion. The proximal portion of the first distal marker is positioned distal of the distal portion of the second distal marker, and the distal portion of the first proximal marker is positioned proximal of the proximal portion of the second proximal marker.

Another aspect of the present disclosure relates to a catheter assembly that includes a stent, a first catheter branch, a second catheter branch, first distal and proximal markers, and second distal and proximal markers. The stent includes a proximal open end, a distal open end, and a side opening defined in a sidewall of the stent at a location between the proximal and distal open ends. The first catheter branch includes a distal end portion that extends in a first direction through the side opening of the stent. The second catheter branch includes a distal end portion that extends through the stent between the distal and proximal open ends. The distal end portion of the first catheter extends in a second direction that is generally the same direction as the first direction prior to insertion of the catheter assembly into a body lumen. The first distal marker and the first proximal marker are positioned on the first catheter branch. At least a portion of the first distal marker is positioned distally of the side opening of the stent and the first proximal marker is positioned proximal of the first distal marker. The second distal marker and the second proximal marker are positioned on the second catheter branch. At least a portion of the second distal marker is positioned further proximally than a proximal portion of the first distal marker, and at least a portion of the second proximal marker is positioned further proximally than a proximal portion of the first proximal member.

Another aspect of the present disclosure relates to a catheter assembly that includes a first catheter branch, a second catheter branch, first distal and proximal markers, and second distal and proximal markers. The first catheter branch includes a distal end portion that extends through the stent. The second catheter branch includes a distal end portion that extends through the stent in an adjacent orientation to the distal end portion of the second catheter branch prior to insertion of the catheter assembly into a body lumen. The first distal marker and the first proximal marker are positioned on the first catheter branch at axially spaced apart locations. The second distal marker and a second proximal marker are positioned on the second catheter branch at axially spaced apart locations. The first distal marker and the first proximal marker each have a length that is imageably distinct from a length of each of the second distal marker and the second proximal marker.

A further aspect of the present disclosure relates to a stent delivery system that includes a stent, a main catheter branch, a side catheter branch, main distal and proximal markers, and side distal and proximal markers. The stent includes a distal open end, a proximal open end, and a side opening defined in a sidewall of the stent at a location between the proximal and distal open ends. The main catheter branch includes a balloon member that extends through the stent from the proximal open end to the distal open end. The main catheter branch is configured to advance over a first guidewire to a main vessel of a vessel bifurcation. The side catheter branch extends into the proximal open end of the stent and extends out of the side opening. The side catheter branch is configured to advance over a second guidewire to a branch vessel of the vessel bifurcation. The main distal marker and the main proximal marker are positioned on the main catheter branch, and the side distal marker and the side proximal marker are positioned on the side catheter branch. At least one of the main and side proximal markers is positioned outside of the stent and at least one of the main and side distal markers are positioned outside of the stent. A relative position of the main and side distal markers and the main and side proximal markers provides an indication of relative twist between the main and side catheter branches and alignment of the stent sidewall opening relative to an opening from the main vessel into the branch vessel of the vessel bifurcation.

A further aspect of the present disclosure relates to a stent delivery system that includes a stent, a main catheter branch, and a side catheter branch. The stent includes a distal open end, a proximal open end, and a side opening at a location between the proximal and distal open ends. The main catheter branch includes a balloon member at least partially positioned within the stent, and the main catheter branch is configured to advance over a first guidewire into a main vessel of a vessel bifurcation. The side catheter branch extends through the side opening of the stent and includes marker material along a length of the side catheter branch. The marker material extends along a distal end portion of the side catheter branch and has a length at least as great as a distance from the side opening of the stent to the distal open end of the stent. The side catheter branch is configured to advance over a second guidewire into a branch vessel of the vessel bifurcation.

A still further aspect of the present disclosure relates to a method of treating a vessel bifurcation. The method includes positioning a first guidewire in a main vessel of the vessel bifurcation, positioning a second guidewire in a branch vessel of the vessel bifurcation, advancing a catheter assembly over the first and second guidewires to the vessel bifurcation, wherein the catheter assembly includes a stent, first and second pairs of markers, and first and second catheter members. The first and second catheter members have a fixed axial position relative to each other, and the first and second catheter members extend through portions of the stent. The method further includes observing relative positions of the first and second pair of markers, adjusting a position of the stent relative to the vessel bifurcation based on observed positions of the first and second pairs of markers; and expanding the stent to treat the vessel bifurcation.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter assembly, comprising:
   a first catheter branch having a distal end portion, the distal end portion of the first catheter branch extending in a first direction;
   a second catheter branch having a distal end portion, the distal end portion of the second catheter branch extending in a second direction that is generally the same direction as the first direction; wherein the first and second catheter branches are secured together at a proximal location and the distal end portions of the first and second catheter branches are free to twist around each other along a longitudinal axis of the catheter assembly;
   a first distal marker and a first proximal marker positioned on the first catheter branch, the first distal marker and the first proximal marker each having a distal portion and a proximal portion;
   a second distal marker and a second proximal marker positioned on the second catheter branch, the second distal marker and the second proximal marker each having a distal portion and a proximal portion, when the first catheter branch and the second catheter branch are in an untwisted configuration, the distal portion of the first proximal marker is positioned proximal of the proximal portion of the second proximal marker and the proximal portion of the first distal marker is positioned distal of the distal portion of the second distal marker; and
   when the first catheter branch and the second catheter branch are in a twisted configuration such that the first catheter branch and the second catheter branch are twisted around one another along a longitudinal axis of the catheter assembly, the proximal portion of the first distal marker is positioned proximal of the distal portion of the second distal marker.

2. The catheter assembly of claim 1, wherein the second catheter branch includes a guidewire shaft that defines a guidewire lumen, an inflation shaft that defines an inflation lumen, and a balloon member coupled in fluid communication with the inflation lumen, and the second proximal and distal markers are positioned on the guidewire shaft.

3. The catheter assembly of claim 1, wherein the first catheter branch includes a guidewire shaft that defines a guidewire lumen, an inflation shaft that defines an inflation lumen, and a balloon member coupled in fluid communication with the inflation lumen, and the first proximal and distal markers are positioned on the guidewire shaft.

4. A catheter assembly, comprising:
   a stent having a proximal open end, a distal open end, and a side opening defined in a sidewall of the stent at a location between the proximal and distal open ends;
   a first catheter branch having a distal end portion, the distal end portion of the first catheter branch extending in a first direction through the side opening of the stent;
   a second catheter branch having a distal end portion, the distal end portion of the second catheter branch extending through the stent between the distal and proximal open ends, the distal end portion of the first catheter branch extending in a second direction that is generally the same direction as the first direction prior to insertion of the catheter assembly into a body lumen, wherein the second catheter branch includes a main balloon and a side balloon for deploying the stent, the side balloon configured to extend radially outward relative to the main balloon; wherein the first and second catheter branches are secured together at a proximal location and the distal end portions of the first and second catheter branches are free to twist around each other along a longitudinal axis of the catheter assembly;

a first distal marker and a first proximal marker positioned on the first catheter branch, the first distal marker positioned distally of the side opening of the stent and the first proximal marker positioned proximal of the first distal marker; and a second distal marker and a second proximal marker positioned on the second catheter branch, the second distal marker positioned proximal of the first distal marker and distal of the first proximal marker, and the second proximal marker positioned proximal of the first proximal member when the first catheter branch and the second catheter branch are in an untwisted configuration and, when the first catheter branch and the second catheter branch are in a twisted configuration such that the first catheter branch is twisted around the second catheter branch and the second catheter branch is twisted around the first catheter branch, the second distal marker is positioned distal of both the first distal marker and the first proximal marker.

5. The catheter assembly of claim 4, wherein at least a portion of the first distal marker is positioned distal of a distal end of the stent, and at least a portion of the first proximal marker is positioned proximal of a proximal end of the stent.

6. The catheter assembly of claim 5, wherein at least a portion of the second distal marker is positioned distal of the distal end of the stent, and at least a portion of the second proximal marker is positioned proximal of the proximal end of the stent.

7. The catheter assembly of claim 4, wherein the first distal marker and the first proximal marker each having a distal portion and a proximal portion, the second distal marker and the second proximal marker each having a distal portion and a proximal portion, the proximal portion of the first distal marker is positioned distal of the distal portion of the second distal marker, and the proximal portion of the first proximal marker is positioned distal of the distal portion of the second proximal marker.

8. The catheter assembly of claim 7, wherein the first distal marker and the first proximal marker are each imageably distinct from the second distal marker and the second proximal marker.

9. The catheter assembly of claim 4, wherein the second distal marker is aligned axially with the side opening of the stent, and at least a portion of one of the first proximal marker and the second proximal marker extends proximal of the proximal open end of the stent.

10. The catheter assembly of claim 4, wherein the second proximal marker is aligned with the side opening of the stent, and at least a portion of each of the first distal marker and the second distal marker extends distally of the distal open end of the stent.

11. The catheter assembly of claim 4, further comprising a first middle marker positioned on the first catheter branch at a location between the first distal marker and the first proximal marker.

12. The catheter assembly of claim 4, further comprising a second middle marker positioned on the second catheter branch at a location between the second distal marker and the second proximal marker.

13. A catheter assembly, comprising:

a first catheter branch having a distal end portion, the distal end portion of the first catheter branch extending through a stent;

a second catheter branch having a distal end portion, the distal end portion of the second catheter branch extending through the stent, the distal end portion of the first catheter branch extending adjacent to the distal end portion of the second catheter branch prior to insertion of the catheter assembly into a body lumen, wherein the first and second catheter branches are secured together at a proximal location and the distal end portions of the first and second catheter branches are free to twist around each other along a longitudinal axis of the catheter assembly;

a first distal marker and a first proximal marker positioned on the first catheter branch at axially spaced apart locations; and a second distal marker and a second proximal marker positioned on the second catheter branch at axially spaced apart locations, the first distal marker and the first proximal marker each having a length imageably distinct from a length of each of the second distal marker and the second proximal marker;

wherein the first distal marker and second distal marker are in a first longitudinal arrangement when the first catheter branch and the second catheter branch are in an untwisted configuration, and the first distal marker and the second distal marker are in a second different longitudinal arrangement when the first catheter branch and the second catheter branch are twisted around one another in a twisted configuration.

14. The catheter assembly of claim 13, wherein the length of the first distal marker and the first proximal marker is at least 25% greater than the length of the second distal marker and the second proximal marker.

15. A stent delivery system, comprising:

a stent having a distal open end, a proximal open end, and a side opening defined in a sidewall of the stent at a location between the proximal and distal open ends;

a main catheter branch, the main catheter branch having a distal end portion including a main balloon member and a side balloon member, the main balloon member extending through the stent from the proximal open end to the distal open end, the side balloon member configured to extend radially outward from the main balloon when inflated, and the main catheter branch configured to advance over a first guidewire to a main vessel of a vessel bifurcation;

a side catheter branch having a distal end portion extending into the proximal open end of the stent and extending out of the side opening, the side catheter branch configured to advance over a second guidewire to a branch vessel of the vessel bifurcation; wherein the main and side catheter branches are secured together at a proximal location and the distal end portions of the main and side catheter branches are free to twist around each other along a longitudinal axis of the stent delivery system;

a main distal marker and a main proximal marker positioned on the main catheter branch; and a side distal marker and a side proximal marker positioned on the side catheter branch, at least one of the main and side proximal markers being positioned outside of the stent and at least one of the main and side distal markers being positioned outside of the stent, and the main and side distal markers and the main and side proximal markers having a first relative position when the main catheter branch and the side catheter branch are untwisted, and the main and side distal markers and the main and side proximal markers having a second relative position when the main catheter branch and the side catheter branch are twisted, wherein when twisted, the main catheter branch and the side catheter branch are twisted around one another along the longitudinal axis.

16. The stent delivery system of claim 15, wherein at least a portion of the side distal marker is positioned distal of a distal portion of the main distal marker when in the first relative position and wherein at least a portion of the side distal marker is positioned proximal of a distal portion of the main distal marker when in the second relative position.

17. The stent delivery system of claim 16, wherein at least a portion of the side proximal marker is positioned further proximally than a proximal portion of the main proximal marker.

18. The stent delivery system of claim 16, wherein relative twist includes twisting of the main and side catheter branches relative to each other at a location between at least the main distal marker and the main proximal marker.

19. A stent delivery system, comprising:
a stent, the stent having a proximal open end, a distal open end, and a side opening defined in a sidewall of the stent at a location between the proximal and distal open ends;
a main catheter branch having a distal portion, the distal portion of the main catheter branch extending through the stent between the proximal and distal open ends of the stent;
the main catheter branch including a first distal marker positioned distal of the stent, and a first proximal marker positioned proximal of the stent;
a side catheter branch having a distal portion, the distal portion of the side catheter branch extending into the stent at a proximal open end of the stent and extending out of the side opening of the stent, the distal portion of the side catheter branch including a distal section extending distally from the side opening of the stent and having a distal end; wherein the main and side catheter branches are secured together at a proximal location and the distal portions of the main and side catheter branches are free to twist around each other along a longitudinal axis of the stent delivery system;
the side catheter branch including a second proximal marker positioned proximal of the stent and a second distal marker on the distal section and positioned distal of the stent;
the first and second proximal markers having a predetermined longitudinal position relative to each other;
the stent delivery system having a first configuration wherein the distal section extends generally parallel with the main catheter branch such that the distal end is in general radial alignment with the side opening in the stent, and when in this first configuration, the first and second distal markers have a first predetermined longitudinal position relative to each other; and
the stent delivery system having a second configuration wherein the distal section and the main catheter branch are twisted about one another such that the distal end is not in general radial alignment with the side opening in the stent, and when in this second configuration, the first and second distal markers are in a second longitudinal position relative to each other that is different from the first predetermined longitudinal position relative to each other.

20. The stent delivery system of claim 19 wherein the first distal marker and the first proximal marker each have a length that is imageably distinct from a length of each of the second distal marker and the second proximal marker.

* * * * *